United States Patent
Nagai

(10) Patent No.: US 9,123,451 B2
(45) Date of Patent: Sep. 1, 2015

(54) IMAGING APPARATUS AND IMAGING METHOD

(75) Inventor: Kentaro Nagai, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 92 days.

(21) Appl. No.: 13/354,121

(22) Filed: Jan. 19, 2012

(65) Prior Publication Data

US 2012/0188556 A1     Jul. 26, 2012

(30) Foreign Application Priority Data

Jan. 25, 2011   (JP) ................. 2011-013256

(51) Int. Cl.
  *G01B 11/02*  (2006.01)
  *G01B 9/02*   (2006.01)
  *G21K 1/06*   (2006.01)
  *A61B 6/00*   (2006.01)

(52) U.S. Cl.
  CPC . *G21K 1/06* (2013.01); *A61B 6/484* (2013.01); *G21K 2207/005* (2013.01)

(58) Field of Classification Search
  CPC ............. G01B 9/02049; G02B 5/1814; G02B 26/0808
  USPC ......................................... 356/511–515, 520
  See application file for complete search history.

(56) References Cited

U.S. PATENT DOCUMENTS

| 7,180,979 B2 | 2/2007 | Momose |
| 7,889,838 B2 | 2/2011 | David et al. |
| 2010/0061508 A1* | 3/2010 | Takahashi ................. 378/36 |
| 2010/0327175 A1* | 12/2010 | Nesterets et al. ............ 250/393 |
| 2012/0008747 A1* | 1/2012 | Roessl et al. .................... 378/87 |
| 2012/0020461 A1* | 1/2012 | Roessl et al. .................... 378/87 |
| 2012/0236985 A1* | 9/2012 | Schusser et al. ................ 378/16 |

FOREIGN PATENT DOCUMENTS

| JP | 2008545981 A | 12/2008 |
| JP | 2010-063646 A | 3/2010 |
| JP | 4445397 B2 | 4/2010 |

* cited by examiner

*Primary Examiner* — Kara E Geisel
*Assistant Examiner* — Hina F Ayub
(74) *Attorney, Agent, or Firm* — Canon USA Inc. IP Division

(57) ABSTRACT

An imaging apparatus includes a diffraction grating configured to produce an interference pattern by diffracting diverging light from a light source, an absorption grating configured to block part of the interference pattern, a detector configured to detect light transmitted through the absorption grating, and a moving unit configured to move the diffraction grating and the absorption grating. The moving unit causes relative movement of the interference pattern and the absorption grating by moving the diffraction grating and the absorption grating such that the diffraction grating and the absorption grating are not moved relative to each other.

16 Claims, 5 Drawing Sheets

IMAGING APPARATUS AND IMAGING METHOD

BACKGROUND OF THE INVENTION

1. Field of the Invention

The present invention relates to imaging apparatuses and imaging methods, and particularly to an imaging apparatus and an imaging method that are capable of imaging a sample using Talbot interferometry.

2. Description of the Related Art

With Talbot interferometry, it is possible to obtain a phase image of a sample using interference of light of various wavelengths, including X-rays. A Talbot interferometer is an instrument that can generate phase images using the Talbot effect.

Examples of methods for imaging a sample using Talbot interferometry include a method in which an imaging apparatus having a source, a diffraction grating, an absorption grating, and a detector is used to obtain a phase image of a sample. An overview of this method will now be described.

First, the incident light from the source is transmitted through the sample and changes its phase. After transmitted through the sample, the light is diffracted by the diffraction grating and forms an interference pattern on a plane apart from the diffraction grating. The interference pattern contains phase information of the sample. When the absorption grating is placed at a position where the interference pattern is formed, the interference pattern is partially blocked and a moiré pattern appears. The moiré pattern is detected by the detector. By computing and analyzing the detection result, a phase image of the sample can be obtained.

There are several ways to obtain a phase image of a sample from the moiré pattern. One of them is a phase stepping method in which an absorption grating is moved relative to an interference pattern to change and detect moiré multiple times, and then the phase is calculated from results of the multiple times of detection.

As a way to move an absorption grating relative to an interference pattern, Japanese Patent No. 4445397 (corresponding to U.S. Pat. No. 7,180,979) describes a method which involves changing a relative position of a diffraction grating and an absorption grating. Also, Japanese Unexamined Patent Application Publication (Translation of PCT Application) No. 2008-545981 (corresponding to U.S. Pat. No. 7,889,838) describes a method which involves moving a light source or source grating configured to split light from the light source into narrow beams.

As described above, Japanese Patent No. 4445397 describes a method in which imaging is performed while the relative position of the diffraction grating and the absorption grating is changed. To carry out this method, it is necessary, each time imaging is performed, to change the relative position of the diffraction grating and the absorption grating by a distance obtained by dividing a period of the absorption grating by the number of times of imaging. For example, when Talbot interferometry is performed using X-rays as light, the moving distance of the diffraction grating or the absorption grating is about several micrometers. Therefore, it is necessary to move the diffraction grating or the absorption grating with high precision such that movement is controlled below the micrometer scale.

Japanese Unexamined Patent Application Publication (Translation of PCT Application) No. 2008-545981 describes a method which involves moving or rotating the source or the source grating. In this method, the moving distance of the source or the source grating for each imaging is about ten times larger than that in the method which involves moving the diffraction grating or the absorption grating.

However, when the source or the source grating is moved, the direction of light incident on a sample is changed with respect to the sample. This is equivalent to a positional displacement between the sample and a detector. Therefore, as the source or the source grating is moved, the light intensity distribution on the detection surface of the detector is displaced and hence, the resulting phase image of the sample may be blurred.

SUMMARY OF THE INVENTION

The present invention provides an imaging apparatus which is capable, in Talbot interferometry, of controlling the movement of a diffraction grating and an absorption grating more easily than in the related art, and performing a phase stepping method while suppressing blurring of a phase image caused by a change in the direction of light incident on a sample.

An imaging apparatus according to an aspect of the present invention includes a diffraction grating configured to produce an interference pattern by diffracting diverging light from a light source, an absorption grating configured to block part of the interference pattern, a detector configured to detect light transmitted through the absorption grating, and a moving unit configured to move the diffraction grating and the absorption grating. The moving unit causes relative movement of the interference pattern and the absorption grating by moving the diffraction grating and the absorption grating such that the diffraction grating and the absorption grating are not moved relative to each other.

Further features of the present invention will become apparent from the following description of exemplary embodiments with reference to the attached drawings.

DESCRIPTION OF THE EMBODIMENTS

Figure 1:
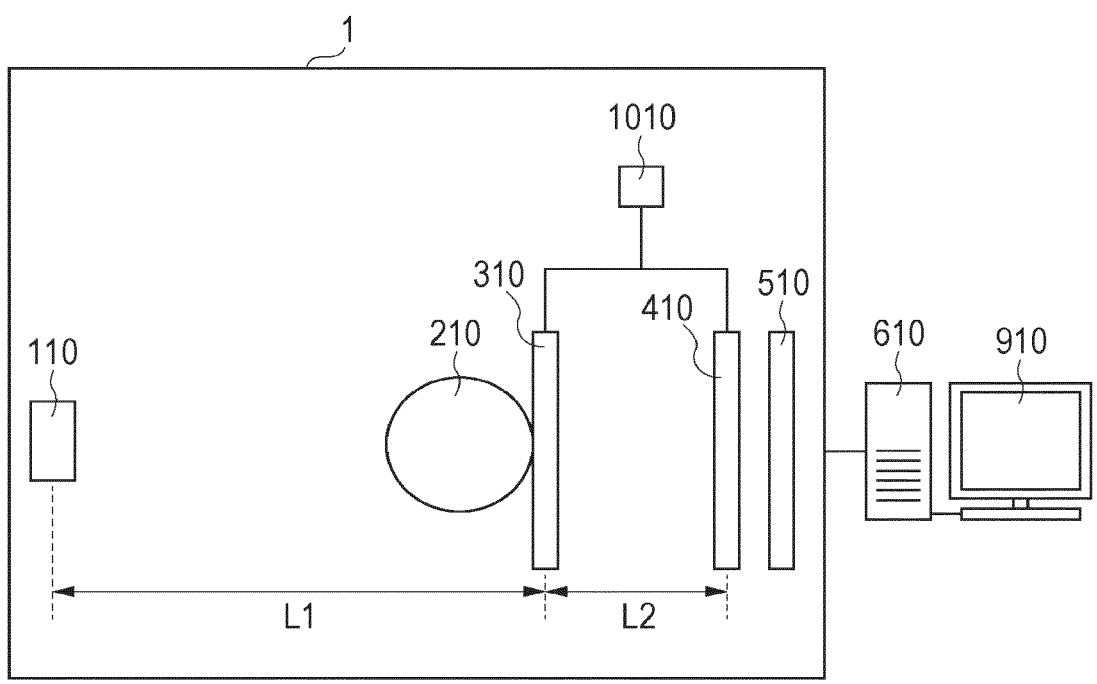
FIG. 1 is a schematic diagram of an X-ray imaging apparatus according to an embodiment of the present invention.

Embodiments of the present invention will now be described with reference to the attached drawings. In the drawings, the same reference numerals are assigned to the same components and redundant description will be omitted.

In the present embodiment, an imaging apparatus will be described which performs Talbot interferometry using X-rays as light. In the present specification, the term X-rays refers to light with an energy of 2 keV to 100 keV.

FIG. 1 is a schematic diagram illustrating a configuration of an imaging apparatus according to the present embodiment. An imaging apparatus 1 illustrated in FIG. 1 includes an X-ray source 110 (source) configured to produce X-rays, a diffraction grating 310 configured to diffract X-rays, an absorption grating 410 configured to block (absorb) part of X-rays, a detector 510 configured to detect X-rays, and a moving unit 1010 configured to move the diffraction grating 310 and the absorption grating 410. A computing unit 610 is connected to the imaging apparatus 1 and an image display unit 910 is connected to the computing unit 610. The computing unit 610 is configured to perform computation on the basis of detection results from the imaging apparatus 1. The image display unit 910 is configured to display an image based on a computation result from the computing unit 610. A configuration of each component will now be described.

The imaging apparatus 1 of the present embodiment includes the X-ray source 110 as a source. An X-ray source that emits either continuous X-rays or characteristic X-rays may be used as the X-ray source 110. A wavelength selection filter or an X-ray source grating (source grating) for splitting X-rays into narrow beams may be provided on the path of X-rays emitted from the X-ray source 110. It is necessary that X-rays emitted from the X-ray source 110 form an interference pattern by being diffracted by the diffraction grating 310. Therefore, the X-rays need to be spatially coherent to a degree which allows formation of an interference pattern. The X-rays emitted from the X-ray source 110 are diverging X-rays (diverging light) which diverge radially from a microsource.

After the X-rays are emitted from the X-ray source 110 and transmitted through a sample 210, the phase of the X-rays is changed depending on the refractive index and shape of the sample 210. Although the sample 210 is placed between the X-ray source 110 and the diffraction grating 310 in FIG. 1, the sample 210 may be placed between the diffraction grating 310 and the absorption grating 410.

The diffraction grating 310 used in the present embodiment is a phase-type diffraction grating (phase grating). The phase-type diffraction grating causes partial phase shift of incident ray. The diffraction grating 310 is irradiated with X-rays and produces an interference pattern in which bright and dark areas are periodically arranged on a plane apart from the diffraction grating. Although an amplitude-type diffraction grating (amplitude grating) may be used as the diffraction grating 310, using a phase-type diffraction grating is advantageous in that the loss of X-rays (light) is smaller. In the present specification, an area with high light intensity is referred to as a bright area, and an area with low light intensity is referred to as a dark area.

Figure 2:
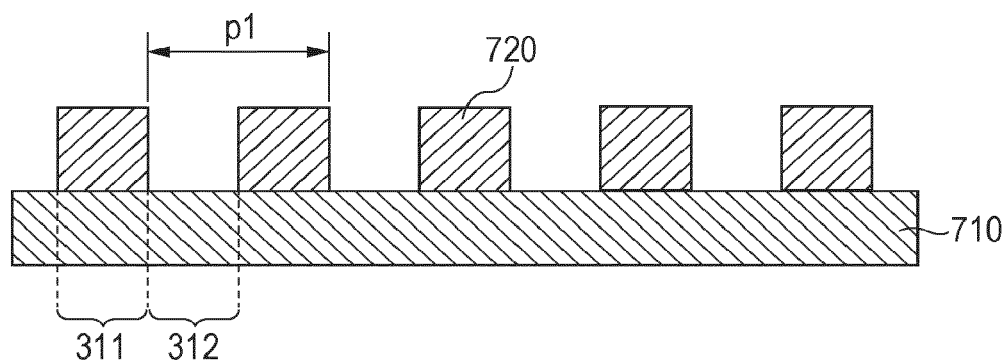
FIG. 2 is a cross-sectional view of a diffraction grating according to an embodiment of the present invention.

FIG. 2 illustrates a cross-sectional shape of the diffraction grating 310 according to the present embodiment. The diffraction grating 310 includes a substrate 710 and structures 720 thereon. The structures 720 are rectangular in cross section and are arranged with a period p1. The diffraction grating 310 has a one-dimensional periodic structure. As viewed from the X-ray source 110, a portion where the structure 720 is present is a phase advance portion 311, and a portion where the structure 720 is not present is a phase delay portion 312. X-rays transmitted through the phase advance portions 311 and X-rays transmitted through the phase delay portions 312 are phase-shifted by a constant amount. A diffraction grating with a phase shift of π radians or π/2 radians is often used, but a diffraction grating with other phase shifts may be used. It is preferable that the diffraction grating 310 be made of material with high X-ray transmittance. For example, silicon may be used to make the diffraction grating 310. The substrate 710 and the structures 720 of rectangular wave shape may be made of the same material. The diffraction grating 310 may have any configuration as long as the phase advance portions 311 and the phase delay portions 312 are periodically arranged. That is, the diffraction grating 310 may have a configuration different from that illustrated in FIG. 2.

The period of an interference pattern is determined by the period p1 and the phase shift of the diffraction grating 310 and the magnification factor of the imaging apparatus 1. The magnification factor indicates the degree to which, when diverging X-rays (diverging light) are used, a pattern produced by the diffraction grating 310 is magnified and projected onto the absorption grating 410. The magnification factor can be expressed as follows:

$$M=(L1+L2)/L1 \quad \text{Expression 1}$$

where M is the magnification factor, L1 is the distance between the X-ray source 110 and the diffraction grating 310, and L2 is the distance between the diffraction grating 310 and the absorption grating 410.

When a phase-type diffraction grating with a phase shift of π radians is used as the diffraction grating 310, the period of the interference pattern on the absorption grating 410 is a value obtained by multiplying the period of the diffraction grating 310 by ½ and the magnification factor M. When a phase-type diffraction grating with a phase shift of π/2 radians is used as the diffraction grating 310, the period of the interference pattern on the absorption grating 410 is a value obtained by multiplying the period of the diffraction grating 310 by the magnification factor M.

Figure 3:
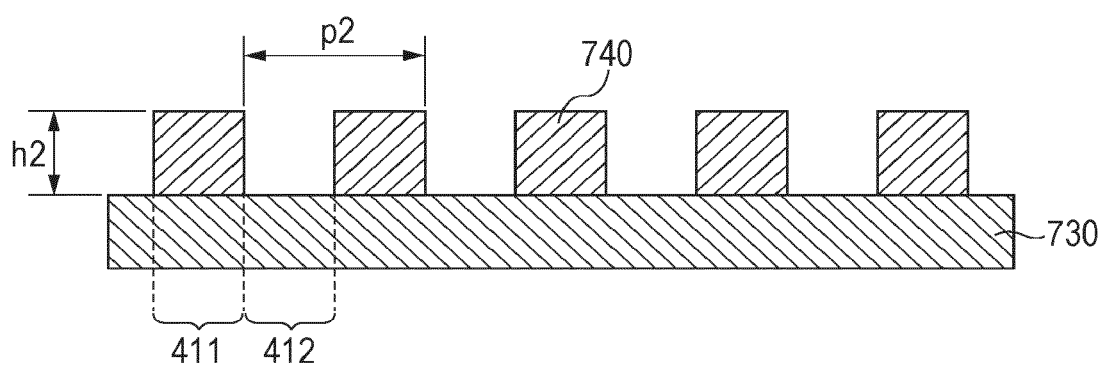
FIG. 3 is a cross-sectional view of an absorption grating according to an embodiment of the present invention.

FIG. 3 illustrates a cross-sectional shape of the absorption grating 410 according to the present embodiment. The absorption grating 410 includes a substrate 730 of high X-ray transmittance and rectangular-wave-shaped structures 740 thereon. For absorbing incident X-rays, it is necessary that the structures 740 be made of material with low X-ray transmittance and have a sufficient height h2. As viewed from the X-ray source 110, a portion where the structure 740 is present is a shield portion 411 that absorbs X-rays, and a portion where the structure 740 is not present is a transmission portion 412 that transmits X-rays. Although the shield portion 411 may not need to completely absorb X-rays, it is necessary that X-rays be absorbed to a degree where moiré is produced by superimposing the absorption grating 410 on the interference pattern. As long as this condition is satisfied, the structures 740 may be of any material and height (h2). The absorption grating 410 may have any configuration as long as the shield portions 411 and the transmission portions 412 are periodically arranged. That is, the absorption grating 410 may have a configuration different from that illustrated in FIG. 3.

A period p2 of the absorption grating 410 can be equivalent to or slightly different from the period of the interference pattern produced by the diffraction grating 310. The period p2 of the absorption grating 410 can be determined depending on the period of moiré desired to be produced.

In the present specification, the term moiré refers to one with an infinite or almost infinite period. That is, the present invention is effective in the case where the period does not clearly appear within a single imaged image, as in an embodiment described in Japanese Patent No. 4445397.

The imaging apparatus 1 of the present embodiment includes the moving unit 1010 that moves the diffraction grating 310 and the absorption grating 410. While maintaining the relative position of the diffraction grating 310 and the absorption grating 410 such that one of the two gratings does not move relative to the other, the moving unit 1010 moves the two gratings in a direction in which bright and dark areas of the interference pattern are arranged. With this moving operation, the interference pattern or the absorption grating 410 moves relative to the other to change the moiré. Therefore, a phase stepping method can be done by carrying out detection before and after the moving operation. A description will now be given of a relationship between the movement of the diffraction grating 310 and the absorption grating 410 and the change of the relative position of the interference pattern and the absorption grating 410.

As described above, while maintaining the relative position of the diffraction grating 310 and the absorption grating 410, the moving unit 1010 of the present embodiment moves the diffraction grating 310 and the absorption grating 410 so as to cause relative movement of the interference pattern and the absorption grating 410. Since the relative position of the diffraction grating 310 and the absorption grating 410 is fixed, no relative movement occurs therebetween. To allow relative movement of the interference pattern and the absorption grating 410 without causing relative movement of the diffraction grating 310 and the absorption grating 410, it is only necessary that the moving velocities of the interference pattern and the absorption grating 410, associated with movement of the diffraction grating 310, be different from each other.

Two exemplary methods of moving the diffraction grating 310 and the absorption grating 410 will now be described.

One is a method in which, along a plane orthogonal to the optical axis, the diffraction grating 310 and the absorption grating 410 are moved in a direction in which bright and dark areas of the interference pattern are arranged. The moving velocities of the diffraction grating 310, the absorption grating 410, and the interference pattern will now be discussed. When the diffraction grating 310 moves at a velocity v1, the absorption grating 410 also moves at the velocity v1 whereas the interference pattern moves at a velocity Mv1 obtained by multiplying the moving velocity of the diffraction grating 310 by the magnification factor M. Therefore, a difference between the moving velocities of the interference pattern and the absorption grating 410 can be expressed as follows:

$$v1 \cdot (M-1) \qquad \text{Expression 2}$$

This results in a change in the relative position of the interference pattern and the absorption grating 410. That is, this causes relative movement of the interference pattern and the absorption grating 410, changes the moiré, and makes it possible to perform a phase stepping method. The moving distance of the diffraction grating 310 and the absorption grating 410 for each detection can be expressed as follows:

$$p2/\{(M-1) \cdot n\} \qquad \text{Expression 3}$$

where n is the number of times of detection.

The other method is one in which, along the circumference of a circle centered on a point, the diffraction grating 310 and the absorption grating 410 are moved in a direction in which bright and dark areas of the interference pattern are arranged. Note that the center of the circle needs to be farther or closer from the diffraction grating 310 than the X-ray source 110. That is, the inequality R>L1 or R<L1 needs to be satisfied, where R is a distance between the center of the circle and the diffraction grating 310, and L1 is a distance between the X-ray source 110 and the diffraction grating 310. Thus, a phase stepping method is made possible, because there is a difference in curvature between the wavefront of X-rays emitted from the X-ray source 110 and the circumference of the circle along which the diffraction grating 310 and the absorption grating 410 are moved. It is preferable that the center of the circumference of the circle along which the diffraction grating 310 and the absorption grating 410 are moved be located on a straight line (optical axis) passing through the center of an X-ray irradiated region of the diffraction grating 310 and the center of the X-ray source 110 (focus).

When the diffraction grating 310 and the absorption grating 410 are moved at an angular velocity θ along the circumference of a circle centered on a point which is located on the optical axis and spaced by the distance R from the diffraction grating 310 toward the X-ray source 110, the moving velocity of the diffraction grating 310 is given by R×θ and the moving velocity of the absorption grating 410 is given by (R+L2)×θ. When v2 is substituted for the moving velocity R×θ of the diffraction grating 310, the moving velocity of the absorption grating 410 is given by v2×(R+L2)÷R. The moving velocity of the interference pattern is given by v2×M. Thus, a difference in moving velocity between the interference pattern and the absorption grating 410 can be expressed as follows:

$$v2\{M-(R+L2)/R\} \qquad \text{Expression 4}$$

Since the distance R is not equal to the distance L1 (R≠L1), the interference pattern and the absorption grating 410 are moved relative to each other and a phase stepping method is made possible. Here, the moving distance of the diffraction grating 310 for each detection can be expressed as follows:

$$p2/\{(M-(R+L2)/R) \cdot n\} \qquad \text{Expression 5}$$

where n is the number of times of detection. This moving distance increases as R approaches L1, and diverges at R=L1.

Although the diffraction grating 310 and the absorption grating 410 are moved by the moving unit 1010 alone in the present embodiment, the moving unit 1010 may include a first moving part and a second moving part configured to move the diffraction grating 310 and the absorption grating 410, respectively. Any configuration is possible as long as the relative position of the diffraction grating 310 and the absorption grating 410 is maintained during detection performed n times. For example, it is possible that after detection, the diffraction grating 310 is moved by the distance given by Expression 5 and then, before the next detection, the absorption grating 410 is moved by the distance obtained by multiplying the distance given by Expression 5 by (R+L2)÷R. However, as compared to an imaging apparatus that performs such a moving operation, another imaging apparatus is more preferable in which the moving unit 1010 moves the diffraction grating 310 and the absorption grating 410 that are integrally configured not to change their relative position. Specifically, it is preferable, for example, that the diffraction grating 310 and the absorption grating 410 be fastened together with screws, bonded together, integrally molded together, or mechanically joined together. Such a configuration of the imaging apparatus 1 can facilitate the movement of the diffraction grating 310 and the absorption grating 410 in a manner such that the diffraction grating 310 and the absorption grating 410 are not moved relative to each other.

The detector 510 includes an imaging device (e.g., a charge-coupled device (CCD) sensor) capable of detecting moiré intensity information of X-rays. The detector 510 detects moiré intensity information in accordance with relative movement of the interference pattern and the absorption grating 410 associated with movement of the diffraction grating 310 and the absorption grating 410. In the present embodiment, intensity information is detected before and after the relative movement of the interference pattern and the absorption grating 410. However, detection of intensity information may not need to be performed for each relative movement of the interference pattern and the absorption grating 410, or may be performed during the relative movement. If the detection is performed during the relative movement, however, the detected moiré intensity distribution may be blurred by the relative movement during the detection. Therefore, it is preferable to shorten the detection time or perform detection after stopping the relative movement of the interference pattern and the absorption grating 410.

Each component of the imaging apparatus 1 according to the present embodiment has been described above.

The computing unit 610 is connected to the imaging apparatus 1 of the present embodiment. The computing unit 610 performs computation on the basis of results of detection performed multiple times by the detector 510. This produces a phase image or a differential phase image of the sample 210. The computing unit 610 is connected to the image display unit 910, which is capable of displaying an image based on the result of computation performed by the computing unit 610.

Specific embodiments and comparative examples will now be described.

First Embodiment

Figure 4A:
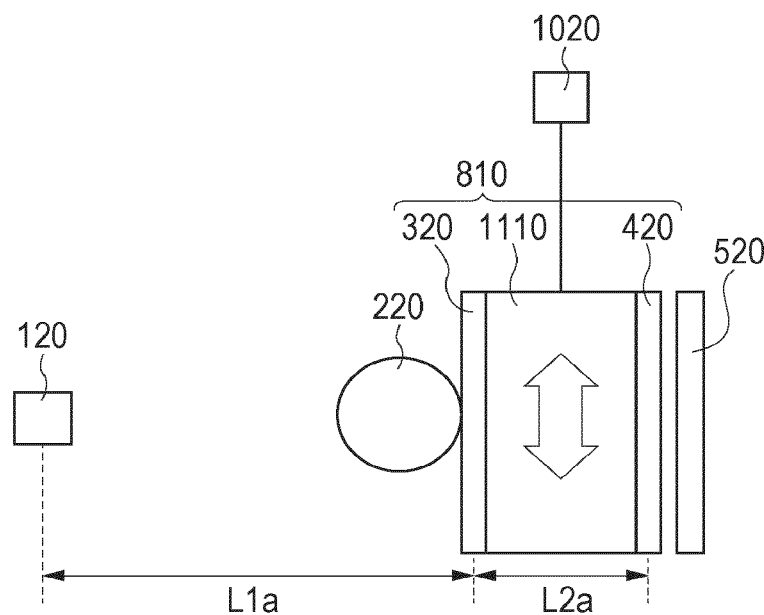
FIG. 4A is a schematic diagram of an X-ray imaging apparatus according to a first embodiment of the present invention, and FIG. 4B a schematic diagram of an X-ray imaging apparatus according to a second embodiment of the present invention.

FIG. 4A illustrates a configuration of an imaging apparatus according to a first embodiment. In the first embodiment, a phase stepping method is performed by moving a diffraction grating 320 and an absorption grating 420 along a plane orthogonal to the optical axis, with the relative position of the diffraction grating 320 and the absorption grating 420 kept constant. Then, the total moving distance of the diffraction grating 320 and the resulting differential phase image of a sample 220 are calculated by simulation. Note that the total moving distance of the diffraction grating 320 is the amount by which the diffraction grating 320 is moved when the displacement of the relative position of the absorption grating 420 and an interference pattern is equal to a distance corresponding to a single period of the absorption grating 420.

An X-ray source 120 is a micro X-ray source with an X-ray producing region (focus) of 10 µm in diameter. The X-ray source 120 produces monochromatic X-rays with an energy of 17.5 keV. The X-rays to be used need to be highly coherent X-rays to produce an interference pattern by being diffracted by the diffraction grating 320. The larger the distance from the X-ray source 120 to the diffraction grating 320, the higher the coherence. In the first embodiment, a distance L1$a$ from the X-ray source 120 to the diffraction grating 320 is set to 1 m. In this configuration, X-rays emitted from the X-ray source 120 can be considered as substantially spherical waves.

The diffraction grating 320 is a phase-type diffraction grating having a one-dimensional periodic structure. The diffraction grating 320 has a configuration similar to that of the diffraction grating 310 having the cross-sectional shape illustrated in FIG. 2. Both the substrate 710 and the rectangular-wave-shaped structures 720 of the diffraction grating 320 are made of silicon. The height of the structures 720 is set to 22.6 µm such that X-rays transmitted through the phase advance portions 311 and X-rays transmitted through the phase delay portions 312 are phase-shifted by $\pi$ radians. A period p1$a$ of the diffraction grating 320 is 8 µm.

When the X-ray source 120 and the diffraction grating 320 described above are used, the interference pattern is produced at a position 12.7 cm away from the diffraction grating 320. The absorption grating 420 is disposed at this position. The interference pattern is a fringe pattern in which bright and dark areas are one-dimensional periodically arranged. In the first embodiment, where the period p1$a$ of the diffraction grating 320 is 8 µm, the phase shift is $\pi$ radians, the distance L1$a$ is 1 m, a distance L2$a$ from the diffraction grating 320 to the absorption grating 420 is 0.127 m, and thus a magnification factor Ma is 1.127, the period of the interference pattern is 8 µm×½×1.127=4.5 µm.

The absorption grating 420 has a one-dimensional periodic structure. The absorption grating 420 has a configuration similar to that of the absorption grating 410 having the cross-sectional shape illustrated in FIG. 3. The substrate 730 of the absorption grating 420 is made of silicon, whereas the rectangular-wave-shaped structures 740 of the absorption grating 420 are made of gold and are 50 µm in height. A period p2$a$ of the absorption grating 420 is 4.5 µm, which is equal to the period of the interference pattern. The absorption grating 420 produces moiré with an infinite period.

A detector 520 has a resolution of 9 µm. On the basis of the results of detection performed by the detector 520, a computing unit performs computation to obtain a phase image of the sample 220.

The imaging apparatus of the first embodiment uses a grating set 810 in which the relative position of the diffraction grating 320 and the absorption grating 420 is fixed by a supporting member 1110. Thus, the relative position of the diffraction grating 320 and the absorption grating 420 is kept constant. For a phase stepping method, a moving unit 1020 moves the grating set 810 along a plane orthogonal to the optical axis.

A silicon sphere of 400 µm in diameter is used as the sample 220 and is placed between the X-ray source 120 and the diffraction grating 320. The closer the sample 220 is to the diffraction grating 320, the more preferable it is. In the first embodiment, the sample 220 is positioned 10 cm in front of the diffraction grating 320.

Figure 5A:
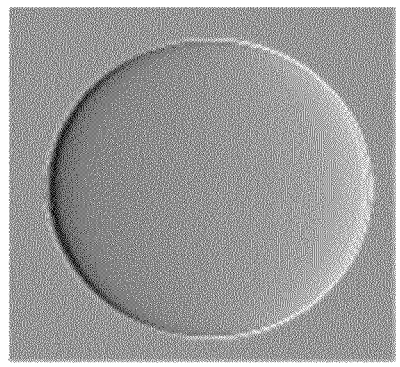
FIG. 5A to FIG. 5E give results of imaging simulations performed using an X-ray imaging apparatus according to an embodiment of the present invention.
Figure 5B:
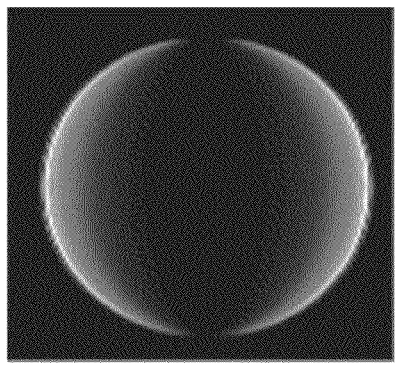
Figure 5C:
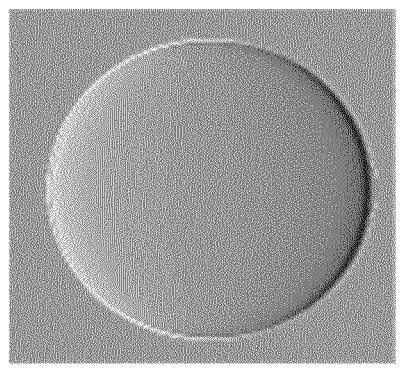
Figure 5D:
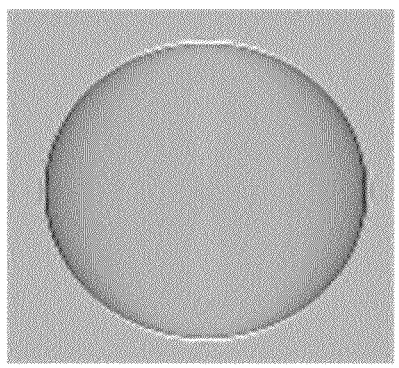
Figure 5E:
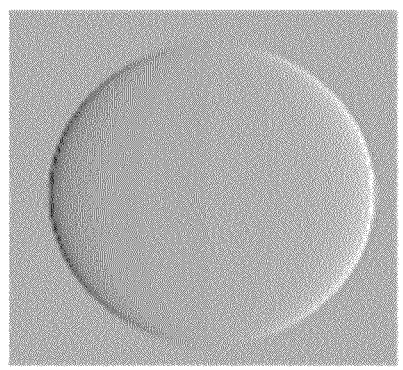

In the imaging apparatus of the first embodiment, X-rays were detected four times during movement of the grating set 810. The detection results are given in FIG. 5A to FIG. 5D. FIG. 5E gives a phase image of the sample 220 calculated from the results of the four times of detection (see FIG. 5A to FIG. 5D). As can be seen, a phase image of the sample 220 can be obtained through phase restoration by performing a phase stepping method using the imaging apparatus of the first embodiment. The total moving distance of the grating set 810 is about 35.5 µm, which is calculated from Expression 3.

Second Embodiment

Figure 4B:
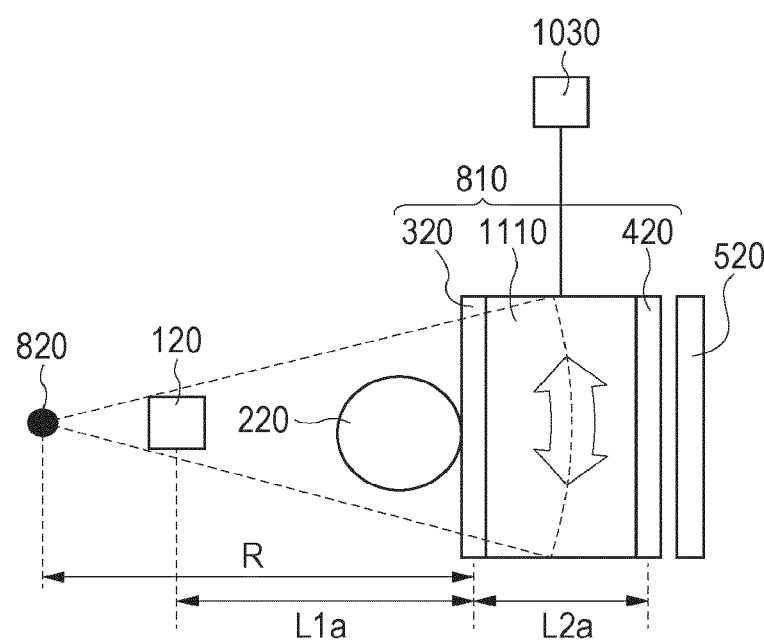

FIG. 4B illustrates a configuration of an imaging apparatus according to a second embodiment. In the second embodiment, unlike the first embodiment in which the grating set 810 is moved along a plane orthogonal to the optical axis, the grating set 810 is slid along the circumference of a circle to perform a phase stepping method. Then, the total moving distance of the diffraction grating 320 is calculated. The second embodiment is the same as the first embodiment, except for a moving unit 1030 and the way in which the grating set 810 is moved.

The distance R from the grating set 810 to a center 820 of the circumference of the circle along which the grating set 810 is moved needs to be larger than, at least, the distance L1$a$ from the grating set 810 to the X-ray source 120. In the second embodiment, the distance R is 2 m and the total moving distance of the diffraction grating 320 of the grating set 810 is about 71.0 µm, which is given by Expression 5. In the second embodiment, where the total moving distance of the diffraction grating 320 is larger than that in the first embodiment, the grating set 810 can be moved more easily than in the first embodiment.

First Comparative Example

Figure 6A:
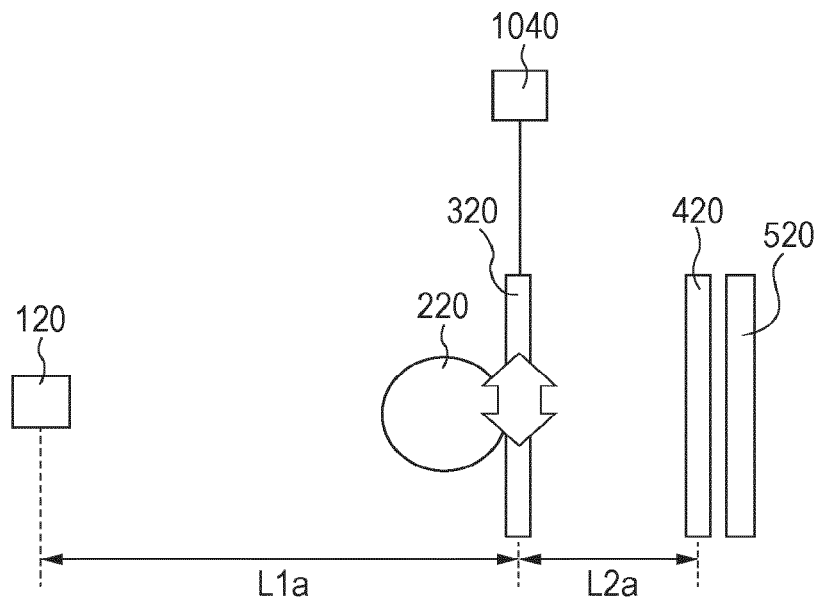
FIG. 6A is a schematic diagram of an X-ray imaging apparatus according to a first comparative example.

FIG. 6A illustrates a configuration of an imaging apparatus according to a first comparative example. In the first comparative example, in accordance with Japanese Patent No. 4445397, the diffraction grating 320 and the absorption grating 420 are moved relative and parallel to each other to perform a phase stepping method, and the total moving distance of the diffraction grating 320 is calculated. In the first comparative example, the absorption grating 420 is fixed and only the diffraction grating 320 is moved by a moving unit 1040. The first comparative example is the same as the first embodiment, except for the moving unit 1040, the way in which the diffraction grating 320 is moved, and the absence of the grating set 810. In the first comparative example, the total moving distance of the diffraction grating 320 is 4.5 µm, as it is equal to the period of the absorption grating 420.

Second Comparative Example

Figure 6B:
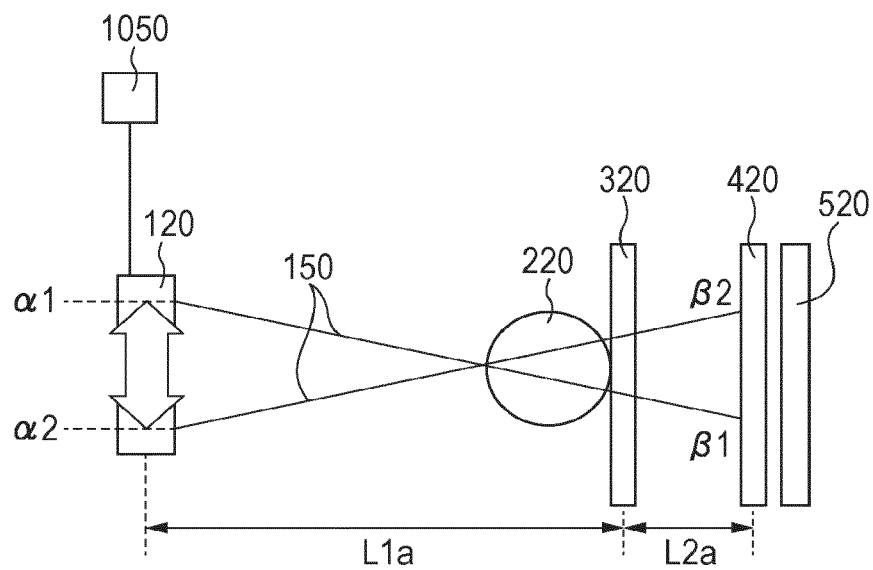
FIG. 6B is a schematic diagram of an X-ray imaging apparatus according to a second comparative example.

FIG. 6B illustrates a configuration of an imaging apparatus according to a second comparative example. In the second comparative example, in accordance with Japanese Unexamined Patent Application Publication (Translation of PCT Application) No. 2008-545981, the X-ray source 120 is moved by a moving unit 1050 to perform a phase stepping method, and the total moving distance of the X-ray source 120 is calculated. The second comparative example is the same as the first embodiment, except for the moving unit 1050 and moving the X-ray source 120 instead of the grating set 810. FIG. 6B illustrates two X-ray sources 120 for describing displacement of an X-ray intensity distribution caused by a change in the incident angle of X-rays 150 incident on the sample 220. However, only one X-ray source 120 is present in the actual configuration, where the X-ray source 120 is moved from α1 to α2 in several steps.

The total moving distance of the diffraction grating 320 is 0 because the diffraction grating 320 is fixed. As described above, the X-ray source 120, instead of the diffraction grating 320, is moved. In the second comparative example, the total moving distance of the X-ray source 120 (i.e., the distance between α1 and α2) is about 35.4 µm, which is given as follows:

$$p2a \cdot (L1a/L2a) \quad \text{Expression 6}$$

Unlike in the cases of the first and second embodiments and the first comparative example, the X-ray source 120 is moved in the second comparative example. This causes a change in the incident angle of the X-rays 150 on the sample 220. The change in the incident angle of the X-rays 150 causes displacement of an X-ray intensity distribution, and hence blurs a phase image of the sample 220 obtained from multiple times of detection. As a result, a microstructure of the sample 220 may not be reproduced.

A description will now be given of displacement of an X-ray intensity distribution caused by a change in the incident angle of the X-rays 150 on the sample 220. When the X-ray source 120 is located at α1, the X-rays 150 incident on the sample 220 at a position closest to the X-ray source 120 are detected at β1 on the detector 520. When the X-ray source 120 is located at α2, the X-rays 150 incident on the sample 220 at the position closest to the X-ray source 120 are detected at β2 on the detector 520. Thus, the X-rays 150 incident on the sample 220 at the same position are detected at different positions β1 and β2 on the detector 520 at the different times of detection. As a result, the distance between the positions β1 and β2 appears as a blur in the resulting phase image of the sample 220.

In the second comparative example, where the sample 220 is located 10 cm in front of the diffraction grating 320, multiple times of movement of the X-ray source 120 results in a displacement of about 8.9 µm on one side of the sample 220 closest to the diffraction grating 320. If the sample 220 is 10 cm thick, the X-rays 150 are incident on the sample 220 at a position 20 cm in front of the diffraction grating 320, the position being on the other side of the sample 220 closest to the X-ray source 120. In this case, the displacement on the one side of the sample 220 closest to the diffraction grating 320 is 14.5 µm. It is possible that such a displacement may affect resolution.

The following table compares the embodiments and comparative examples described above.

TABLE 1

| | Total Moving Distance of Diffraction Grating in Phase Stepping Method | Displacement in Sample Caused by Movement of X-Ray Source |
|---|---|---|
| First Embodiment | 35.5 µm | None |
| Second Embodiment | 71.0 µm | None |
| First Comparative Example | 4.5 µm | None |
| Second Comparative Example | 35.4 µm (total moving distance of X-ray source) | 14.5 µm (maximum) |

In Table 1, the total moving distance indicates the amount by which the diffraction grating 320 or the X-ray source 120 is moved to change the relative position of the absorption grating 420 and the interference pattern by 4.5 µm. The moving distance of the diffraction grating 320 or the X-ray source 120 for each detection is obtained by dividing the total moving distance by the number of times of detection. If, as in the first embodiment, detection is performed four times in the second embodiment and the first and second comparative examples, the moving distance of the diffraction grating 320 or the X-ray source 120 for each detection is one-quarter of the total moving distance in Table 1. The smaller the moving distance, the more precision is required in positioning the diffraction grating 320 or the X-ray source 120.

This will be described with an example. To change the relative position of the absorption grating 420 and the interference pattern by 4.5 µm, the diffraction grating 320 and the absorption grating 420 are moved by 35.5 µm in the first embodiment and the diffraction grating 320 is moved by 4.5 µm in the first comparative example. In the first embodiment, if the moving distance of the diffraction grating 320 and the absorption grating 420 deviates by 1 µm from a desired moving distance, the moving distance of the absorption grating 420 and the interference pattern deviates by 35.5 µm÷4.5≈0.13 µm from a desired moving distance. In the first comparative example, on the other hand, if the moving distance of the diffraction grating 320 deviates by 1 µm from a desired moving distance, the moving distance of the absorption grating 420 and the interference pattern also deviates by 4.5 µm÷4.5=1 µm from a desired moving distance. Thus, in the first and second embodiments and the second comparative example, as compared to the first comparative example, the error in the moving distance of the diffraction grating 320 or the X-ray source 120 less easily appears as an error in the relative moving distance of the interference pattern and the absorption grating 420, and hence the level of precision required in positioning is lower. Although the total moving distance has been used for illustrative purposes, the same applies to the moving distance for each detection. That is, in the first and second embodiments and the second comparative example, as compared to the first comparative example, an error in the moving distance of the diffraction grating 320 or the X-ray source 120 for each detection less easily appears as an error in the relative moving distance of the interference pattern and the absorption grating 420 for each detection.

Table 1 indicates that as compared to the first comparative example, the total moving distances in the first and second embodiments are about ten times larger and hence the diffraction grating 320 and the absorption grating 420 can be moved more easily. As for the second comparative example, where the X-ray source 120 is moved and the incident angle of X-rays on the sample 220 is varied, the resulting phase image of the sample 220 is blurred and hence the resolution is limited, as compared to those in the first and second embodiments. In the first and second embodiments described above, it is possible to provide a phase stepping method in which the diffraction grating 320 and the absorption grating 420 can be easily moved and the phase image of the sample 220 is free of blurring caused by a change in the incident angle (incident wavefront) of X-rays on the sample 220.

Although the imaging apparatus using X-rays has been described in the embodiments, other types of light, such as ultraviolet rays or visible light, may be used in the present invention.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-013256 filed Jan. 25, 2011, which is hereby incorporated by reference herein in its entirety.

What is claimed is:

1. A Talbot interferometer comprising:
a diffraction grating configured to produce an interference pattern by diffracting diverging light from a light source;
an absorption grating configured to block part of the interference pattern;
a detector configured to detect light transmitted through the absorption grating, wherein the detector performs a first detection and a second detection; and
a computing unit configured to obtain information of a sample based on detection results obtained by the detector in the first detection and the second detection,
wherein the diffraction grating and the absorption grating move by translational movement along a plane which intersects an optical axis such that the diffraction grating and the absorption grating are displaced away from or towards the optical axis for a same distance in a period of time between the first detection and the second detection, while the detector is stationary.

2. The Talbot interferometer according to claim 1, wherein the diffraction grating and the absorption grating are configured integrally with each other.

3. The Talbot interferometer according to claim 1, wherein the diffraction grating and the absorption grating move by translational movement in a direction in which bright and dark areas of the interference pattern are arranged.

4. An imaging method comprising:
generating, with a diffraction grating, an interference pattern by diffracting diverging light from a light source;
blocking, with an absorption grating, part of the interference pattern;
detecting light transmitted through the absorption grating by using a detector configured to detect light, wherein the detector performs a first detection and a second detection; and
causing relative movement of the interference pattern and the absorption grating by moving the diffraction grating and the absorption grating by translational movement along a plane which intersects an optical axis such that the diffraction grating and the absorption grating are displaced away from or towards the optical axis for a same distance in a period of time between the first detection and the second detection, while the detector is stationary.

5. The imaging method according to claim 4, wherein causing relative movement of the interference pattern and the absorption grating includes moving by the translational movement the diffraction grating and the absorption grating in a direction orthogonal to the optical axis.

6. The Talbot interferometer according to claim 1,
wherein the computing unit obtains information of the sample based on results of detection performed multiple times by the detector.

7. An imaging method comprising:
generating, with a diffraction grating, an interference pattern by diffracting diverging light from a light source;
blocking, with an absorption grating, part of the interference pattern;
detecting light transmitted through the absorption grating by using a detector configured to detect light, wherein the detector performs a first detection and a second detection; and
causing relative movement of the interference pattern and the absorption grating, by moving the diffraction grating and the absorption grating by movement along a curved trajectory which crosses an optical axis, such that the diffraction grating and the absorption grating are displaced away from or towards the optical axis for a same angle along the curved trajectory in a period of time between the first detection and the second detection,
wherein the curved trajectory intersects a circumference of a circle which is centered on a focus of the light source.

8. A Talbot interferometer comprising:
a diffraction grating configured to produce an interference pattern by diffracting diverging light from a light source;
an absorption grating configured to block part of the interference pattern;
a detector configured to detect light transmitted through the absorption grating, wherein the detector performs a first detection and a second detection; and
a computing unit configured to obtain information of a sample based on detection results obtained by the detector in the first detection and the second detection,
wherein the diffraction grating and the absorption grating move by movement along a curved trajectory which crosses an optical axis, such that the diffraction grating and the absorption grating are displaced away from or towards the optical axis for a same angle along the curved trajectory in a period of time between the first detection and the second detection,
wherein the curved trajectory intersects a circumference of a circle which is centered on a focus of the light source.

9. The Talbot interferometer according to claim 8, wherein the diffraction grating and the absorption grating are configured integrally with each other.

10. The Talbot interferometer according to claim 8, wherein the diffraction grating and the absorption grating move in a direction in which bright and dark areas of the interference pattern are arranged.

11. The Talbot interferometer according to claim 8,
wherein the computing unit obtains information the sample based on results of detection performed multiple times by the detector.

12. The Talbot interferometer according to claim 8,
wherein the diffraction grating and the absorption grating move together such that a relative position of the diffraction grating and the absorption grating at the first detection and at the second detection is kept constant.

13. The Talbot interferometer according to claim 8,
wherein the curved trajectory follows a circumference of a circle centered on a point which does not correspond to the focus of the light source.

14. The Talbot interferometer according to claim 13,
wherein a distance from the diffraction grating to the center of the circle located on the optical axis is larger than a distance from the diffraction grating to the light source.

15. The Talbot interferometer according to claim 13,
wherein the point is located on the optical axis.

16. The Talbot interferometer according to claim 8,
wherein a relative position of the focus, the diffraction grating and the absorption grating changes in the period between the first detection and the second detection.

* * * * *